US00PP15506P2

(12) United States Plant Patent
Olesen et al.

(10) Patent No.: US PP15,506 P2
(45) Date of Patent: Feb. 1, 2005

(54) MINIATURE ROSE VARIETY 'POULRA21'

(50) Latin Name: *Rosa hybrida*
Varietal Denomination: POULra021

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 99 days.

(21) Appl. No.: 10/336,052

(22) Filed: Jan. 3, 2003

(51) Int. Cl.[7] ..... A01H 5/00
(52) U.S. Cl. ..... Plt./107
(58) Field of Search ..... Plt./107

(56) References Cited

U.S. PATENT DOCUMENTS

PP11,242 P * 2/2000 Kordes ..... Plt./116

PP13,454 P3 * 1/2003 Olesen et al. ..... Plt./116

OTHER PUBLICATIONS

UPOV ROM GTITM Computer Database, GTI JOUVE Retrieval Software 2003/01 citation(s) for 'POULra021'.*

* cited by examiner

*Primary Examiner*—Bruce R. Campell

*Assistant Examiner*—W C Haas

(57) ABSTRACT

A new miniature rose plant which has abundant, pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULra021'.

SUMMARY OF THE INVENTION

The present invention constitutes a new and distinct variety of miniature rose plant which originated from a controlled crossing between 'POULsabel', described and illustrated in U.S. Plant patent application Ser. No. 10/136,451 filed on Apr. 29, 2002 and 'KORstoffein' described and illustrated in U.S. Plant Pat. No. 11,242, issued on Feb. 22, 2002. The two parents were crossed and the resulting seeds were planted in a controlled environment. The new variety is named 'POULra021'.

The new rose may be distinguished from its seed parent, 'POULsabel', by the following combination of characteristics:

1. 'POULsabel' has a petal count of 30 to 35, while 'POULra021' has a petal count of 35 to 45.
2. 'POULsabel' has a general tonality of Red Group 53A, while 'POULra021'has a general tonality of Red Group 49B.
3. 'POULsabel' has a thorn color of Greyed-Purple Group 185B.

The new variety may be distinguished from its pollen parent, 'KORstoffein' created by the same inventors, by the following combination of characteristics:

1. 'KORstoffein' has a petal count of 25 to 30 petals; 'POULra021' has a petal count of 35 to 45.
2. 'KORstoffein' has blooms with a yellow-blend coloration, while the coloration of 'POULra021' is pink.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULra021' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULra021' was selected by the inventors as a single plant from the progeny of the hybridization in Spring of 1999.

Asexual reproduction of 'POULra021' by cuttings and traditional budding was first done by L. Pernille and Mogens N. Olesen in their nursery in Fredensborg, Denmark in July of 1999. This initial and other subsequent propagations conducted in controlled environments have demonstrated that the characteristics of 'POULra021' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra021'. Specifically illustrated in the drawing:

1. Stem showing branching and the attachment of leaves, buds, and peduncles;
2. Flower bud, partially opened bud, and open bloom;
3. Flower petals, detached;
4. Sepals, receptacle, and pedicel;
5. Stem as well as a bare stem exhibiting thorns;
6. Leaves.

DETAILED DESCRIPTION OF THE VARIETY

Figure 1:
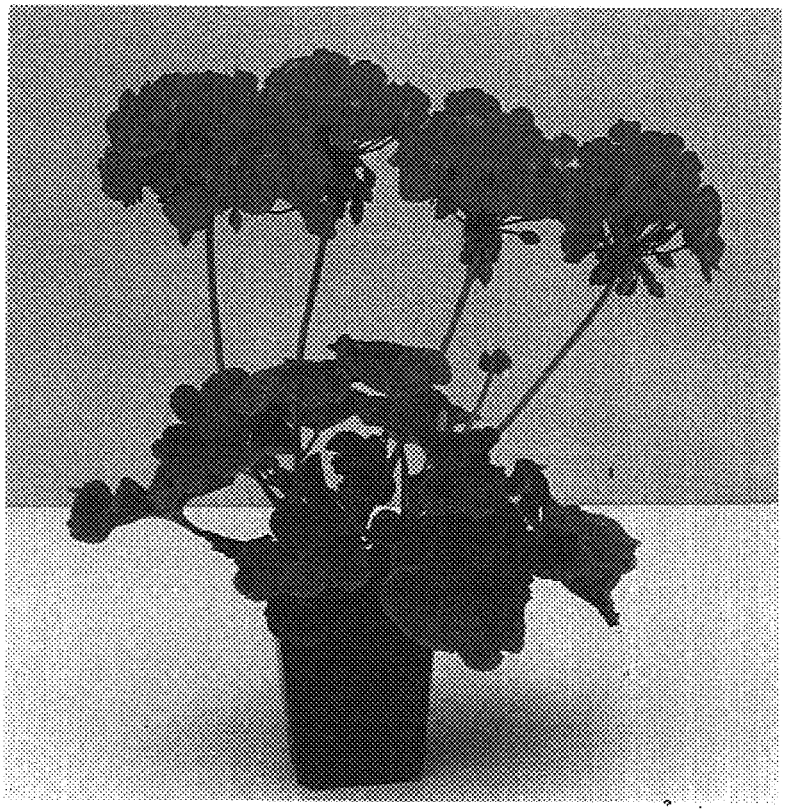
Figure 2:
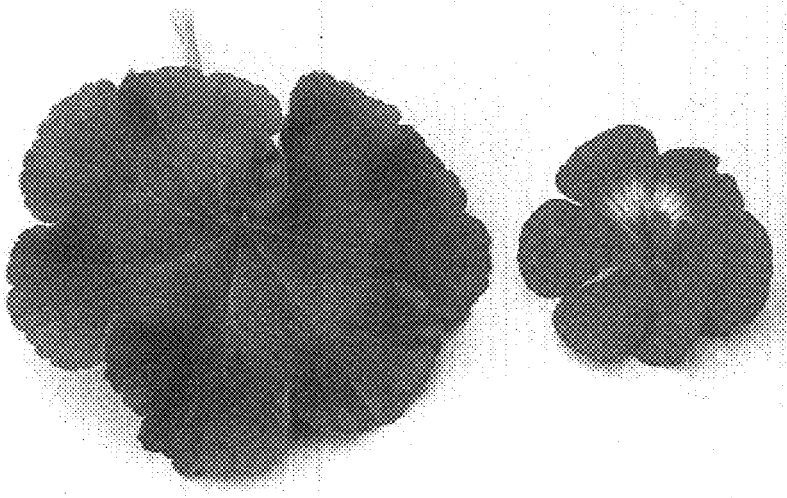

The following is a description of 'POULra021', as observed in its growth in a glasshouse in Burlington, Canada. Observed plants are 10 weeks of age. Color references are made using The Royal Horticultural Society (London, England) Colour Chart, 1995, except where common terms of color are used.

For a comparison, several physical characteristics of the rose variety 'POULra004', a rose variety from the same inventors described and illustrated in U.S. Plant Pat. No. 13,454, dated Jan. 7, 2003, are compared to 'POULra021' in Chart 1.

CHART 1

| | 'POULra021' | 'POULra004' |
|---|---|---|
| Bud color | Red Group 55B. | Red Group 38B. |
| Petal Count | 35 to 45. | 40 to 50. |
| Bloom diameter | 35 to 40 mm. | 45 to 50 mm. |

Parents: 'POULsabel'×'KORstoffein'.

Classification:

*Botanical.*—*Rosa hybrida.*

*Commercial.*—Miniature.

FLOWER AND FLOWER BUD

Blooming habit: Continuous.

Flower bud:

*Size.*—Upon opening, 20 mm in length from base of receptacle to end of bud. Bud diameter is 9 to 10 mm.

*Bud form.*—Long and broad-based.

*Bud color.*—As sepals unfold, Red Group 55B. At ¼ opening, Red Group 55B.

*Sepals.*—Upper surface: Yellow-Green Group 144A and B. Lower surface: Yellow-Green Group 144A. Weak foliaceous appendages on three of the five sepals. Surfaces of sepals moderately pubescent. Stipitate glands are present on edges of sepals. Shape: Sepal base is flat with union of receptacle. Sepal apex is ensiform. Overall, sepal shape is characterized as subulate. Margin: Margins are entire with moderate foliaceous appendages, protruding 3 to 5 mm. Size: 18 to 20 mm long×5 to 7 mm wide.

*Receptacle.*—Surface: Smooth. Shape: Funnel-shaped. Size: 5 mm (h)×8 mm (w). Color: Yellow-Green Group 144A.

*Peduncle.*—Surface: With stipitate glands. Length: 15 to 20 mm average length. Diameter: 3 mm. Color: Yellow-Green Group 144A and B. Strength: Somewhat strong.

*Borne.*—Singly.

*Anthocyanin.*—Greyed-Red Group 182A.

Flower bloom:

*Fragrance.*—None.

*Duration.*—As a pot plant, flowers last from 10 to 14 days.

*Size.*—Medium for a 10 cm pot rose. Average flower diameter is 35 to 40 mm when open. Flower depth is 22 mm.

*Form.*—Shape of flower when viewed from the side: Upon opening, upper part: Flat. Upon opening, lower part: Flattened convex. Open flower, upper part: Flattened convex. Open flower, lower part: Concave.

*Petalage.*—Average range: 35 to 45 petals under normal conditions with 4 to 6 petaloids.

Color:

*Upon opening, petals.*—Outermost petals: Outer Side: Red Group 48A and B. Inner Side: Red Group 48B and C. Innermost petals: Outer Side: Red Group 48A and B. Inner Side: Red Group 48B and C.

*Upon opening, basal petal spots.*—Outermost petals: Outer Side: Green-White Group 157C. Inner Side: Green-White Group 157C. Innermost petals: Outer Side: Green-White Group 157C. Inner Side: Green-White Group 157C.

*After opening, petals.*—Outermost petals: Outer Side: Red Group 49 A and B. Inner Side: Red Group 49 B and C. Innermost petals: Outer Side: Red Group 49 A and B. Inner Side: Red Group 49 B and C.

*After opening, basal petal spots.*—Outermost petals: Outer Side: Green-White Group 157C. Inner Side: Green-White Group 157C. Innermost petals: Outer Side: Green-White Group 157C. Inner Side: Green-White Group 157C.

General tonality: On open flower Red Group 49B. No change in the general tonality at the end of the 5th day. Afterwards, general tonality is Red Group 49B.

Petals:

*Petal reflex.*—Moderate.

*Petal edge.*—Entire.

*Shape.*—Round.

*Size.*—19 mm in length by 17 mm wide.

*Petaloids.*—Quantity: 2 to 4. Size: 10 mm long; 8 mm wide. Shape: Elliptic and irregular. Color: Red Group 55C and D on the upper surface; Red Group 55D on lower surface.

*Thickness.*—Moderate.

*Arrangement.*—Not formal.

Reproductive organs:

*Pistils.*—Length: 6 mm long. Quantity: 20 to 25. Color: Greyed-Purple 184B.

*Pollen.*—None observed.

*Anthers.*—Size: 1 mm long. Color: Greyed-Orange Group 162A. Quantity: 20 to 25.

*Filaments.*—Color: Yellow Group 3C. Length: 5 mm.

*Stigmas.*—Slightly inferior in location to anthers. Color: Greyed-Purple Group 184B.

*Styles.*—Color: Greyed-Purple Group 184B.

*Seed formation.*—No hips observed.

PLANT

Plant growth: Vigorous and upright. When grown as a 10 cm pot plant, the average height of the plant itself is 20 cm and the average width is 18 cm.

Stems:

*Color.*—Young wood: Yellow-Green Group 144B. Older wood: Yellow-Green Group 144B.

*Length.*—14 cm.

*Diameter.*—3 to 4 mm.

*Internodal distance.*—15 to 17 mm.

*Prickles.*—Incidence: None.

*Surface.*—Young wood: Smooth. Older wood: Smooth.

Plant foliage: Normal number of leaflets on leaves in middle of the stem: 5 leaflets.

*Leaf size.*—65 mm (l)×45 mm (w).

*Quantity.*—6 compound leaves per 10 cm stem.

*Color.*—Upper Leaf Surface: Green Group 137A. Lower Leaf Surface: Green Group 138B. Juvenile foliage: Upper Leaf Surface: Green Group 137A. Lower Leaf Surface: Green Group 138B. Anthocyanin intonation: Location: Juvenile leaflet margins and undersides may exhibit intonations of Greyed-Purple Group 187B.

Plant leaves and leaflets:

*Stipules.*—Stipitate glands present on edges. Shape: Narrow at center with lobes of apecies turned outward. Margins are entire. Size: 9 mm long. Color: Yellow-Green Group 144A. Anthocyanin: Present on stipule edges. Greyed-Reed Group 181A.

*Petiole.*—Length: 10 mm long. Diameter: 2 mm. Color: Green Group 137A. Underneath: Yellow-Green Group 144A. With a single, small thorn. Margins: Green Group 137A. With stipitate glands.

*Leaflet.*—Edge: Finely serrated. Shape: Ovate. Apex shape is mucronate. Base shape is rounded. Size: 28 mm in length by 18 mm wide. Vein color: Yellow-Green Group 151A. Texture: Thin. Glossiness: Matte. Arrangement: Odd pinnate. Venation: Reticulate.

Disease resistance: Average resistance to mildew, black spot, and Botrytis under normal growing conditions in Burlington, Canada.

It is claimed:

1. A new and distinct variety of rose plant of the miniature class, substantially as herein illustrated and described as a distinct and novel rose variety due to its abundant, pink flowers, vigorous growth, compact habit, suitability for production from softwood cuttings in pots, and durable flowers and foliage which make the variety suitable for distribution in the floral industry.

* * * * *